US012699051B2

(12) United States Patent
Bózsik et al.

(10) Patent No.: US 12,699,051 B2
(45) Date of Patent: Aug. 4, 2026

(54) MICROSCOPE FOR HIGH-RESOLUTION AND SPECIFIC ANALYSIS OF BIOLOGICAL SUBSTANCES, AND METHOD OF ANALYSIS

(71) Applicant: LYME DIAGNOSTICS KFT., Budakalász (HU)

(72) Inventors: Béla Pál Bózsik, Budapest (HU); Béla Bózsik, Budapest (HU); András Pál Bózsik, Budakalász (HU)

(73) Assignee: LYME DIAGNOSTICS KFT., Budakalász (HU)

( * ) Notice: Subject to any disclaimer, the term of this patent is extended or adjusted under 35 U.S.C. 154(b) by 931 days.

(21) Appl. No.: 17/792,061

(22) PCT Filed: Jun. 30, 2020

(86) PCT No.: PCT/HU2020/000022
§ 371 (c)(1),
(2) Date: Jul. 11, 2022

(87) PCT Pub. No.: WO2021/144596
PCT Pub. Date: Jul. 22, 2021

(65) Prior Publication Data
US 2023/0085045 A1 Mar. 16, 2023

(30) Foreign Application Priority Data
Jan. 13, 2020 (HU) ................................... P2000014

(51) Int. Cl.
*G01N 21/64* (2006.01)
*G01N 33/569* (2006.01)
(Continued)

(52) U.S. Cl.
CPC ..... *G01N 21/6458* (2013.01); *G01N 21/6428* (2013.01); *G01N 33/56911* (2013.01);
(Continued)

(58) Field of Classification Search
CPC ........... G01N 21/6458; G01N 21/6428; G01N 33/56911; G01N 2021/6439; G02B 21/10;
(Continued)

(56) References Cited

U.S. PATENT DOCUMENTS

| | | | | |
|---|---|---|---|---|
| 4,027,161 | A * | 5/1977 | Williams | ........... G01B 11/0691 |
| | | | | 250/353 |
| 6,859,581 | B1 * | 2/2005 | Smith | ....................... G01J 3/02 |
| | | | | 398/79 |
| 2007/0014002 | A1 * | 1/2007 | Vodyanoy | ............ G02B 21/125 |
| | | | | 359/368 |

FOREIGN PATENT DOCUMENTS

| | | | |
|---|---|---|---|
| DE | 102012207217 A1 | 10/2013 | |
| EP | 1598688 A2 | 11/2005 | |

(Continued)

OTHER PUBLICATIONS

Thorlabs, "Mounted LEDs", Thorlabs, Mar. 22, 2016, Retrieved Feb. 27, 2025. Retrieved from Internet Archive:https://web.archive.org/web/20160322104007/http://www.thorlabs.com/newgrouppage9.cfm?objectgroup_ID=2692 (Year: 2016).*

(Continued)

*Primary Examiner* — Bumsuk Won
*Assistant Examiner* — Ray Alexander Dean
(74) *Attorney, Agent, or Firm* — Csaba Henter; MILLEN, WHITE, ZELANO & BRANIGAN, P.C.

(57) ABSTRACT

The subject of the invention is a microscope for high-resolution and specific analysis of biological substances. The microscope according to the invention is characterized by a power supply unit capable of generating constant current attached to the microscope housing; a set of mirrors and illuminating optics; a collimator placed between a monochromatic light source emitting light in a very narrow range of wavelengths and the collector lens; a dark-field condenser and objective including an in-between space to (Continued)

Figure 1:
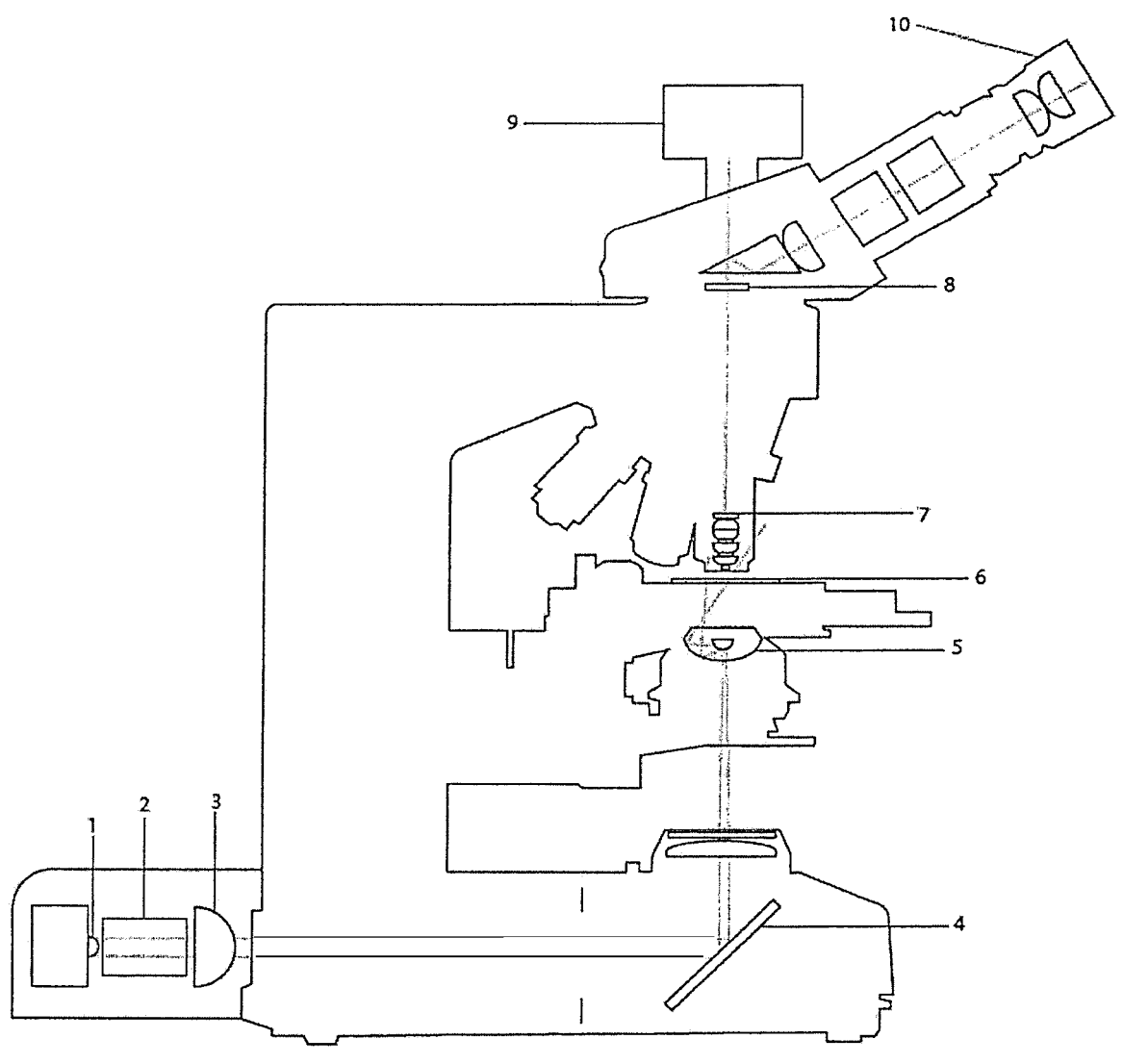

accommodate the stained biological specimen; and a surveillance camera or eyepiece, and a removable color filter placed between the objective and the surveillance camera or the eyepiece.

The invention also covers the method to analyze biological specimens with fluorescent staining, wherein the biological contents of the specimen are analyzed in a growing medium in liquid state after the addition of antibodies marked with fluorescent stain, using the microscope according to the invention.

The microscope according to the invention enables up to one order of magnitude higher resolution than conventional light microscopes and 10-30% higher resolution compared to currently used dark-field microscopes and provides a remarkably sharper camera image.

14 Claims, 2 Drawing Sheets

(51) Int. Cl.
 *G02B 21/10* (2006.01)
 *G02B 21/16* (2006.01)

(52) U.S. Cl.
 CPC ............. *G02B 21/10* (2013.01); *G02B 21/16* (2013.01); *G01N 2021/6439* (2013.01)

(58) Field of Classification Search
 CPC ...... G02B 21/16; G02B 21/361; G02B 27/58; G02B 21/00; G02B 21/06; B29D 11/00; F21V 1/00
 See application file for complete search history.

(56) References Cited

FOREIGN PATENT DOCUMENTS

| | | | |
|---|---|---|---|
| GB | 1257382 | A | 12/1971 |
| JP | 2002-131648 | A | 5/2002 |
| WO | 2012/047678 | A2 | 4/2012 |
| WO | 2016/138064 | A1 | 9/2016 |

OTHER PUBLICATIONS

Davidson, Optical Microscopy: Fluorescence Microscopy: Transmitted Light Illumination, Molecular Expressions, Sep. 5, 2015, retrieved Feb. 26, 2025. Retrieved from Internet Archive: https://web.archive.org/web/20150905124337/http://micro.magnet.fsu.edu/primer/techniques/fluorscence/anatomy/translighpath (Year: 2015).*

Davidson, Optical Microscopy Anatomy of the Fluorescence Microscope, Molecular Expressions, Mar. 3, 2011, retrieved Feb. 26, 2025. Retrieved from Internet Archive: https://web.archive.org/web/20110303201209/https://micro.magnet.fsu.edu/primer/technique/fluorescence/anatomy/fluoromicroanatomy.html (Year: 2011).*

"How to obtain the best resolution with your microscope". Microbehunter Microscopy, http://www.microbehunter.com/how-to-obtain-the-best-resolution-with-your-microscope/, published Mar. 28, 2014. The publication date indicated herein is the earliest known publication date.

"LED Light Source for Microscopy" Data Sheet, Bluebox Optics Ltd., dated Jun. 2019, 4 pp., https://blueboxoptics.com/wp-content/uploads/2019/06/niji-datasheet-BBO-NIJI-JUN-19-A.pdf.

"Resolution and Imaging", University of Cambridge, Optical Microscopy and Specimen Preparation, 3 pp., https://www.doitpoms.ac.uk/tlplib/optical-microscopy/resolution.php, published Oct. 13, 2004. The publication date indicated herein is the earliest known publication date.

Authorized Officer: Windecker, Robert, International Search Report and Written Opinion issued in PCT application No. PCT/HU2020/000022, Oct. 15, 2020, 12 pp.

BME MOGI Department, Technical Optics, Chapter 7—"The microscope as an optical system", http://mogi.bme.hu/TAMOP/muszaki_optika/ch07.html#ch-VII.I.16, dated 2015.

Contributing Author: Michael W. Davidson, "Education in Microscopy and Digital Imaging ZEISS Microscopy Online Campus, Light-Emitting Diodes", 15 pp., published Dec. 20, 2008, http://zeiss-campus.magnet.fsu.edu/articles/lightsources/leds.html. The publication date indicated herein is the earliest known publication date.

David Selmeczi, Fluorescent staining, May 18, 2001, http://selmeczi.eu/david/diploma/diplomamunkanode19.html.

Dr. Miklos Kellermayer, "Biomedical light microscopy and computer image analysis", Ph.D. course 1311, Doctoral School of Theoretical Medicine, Semmelweis University, dated 2010, 66 pp.

Joseph Sinko, "Examination and correction of rendering and image reconstruction errors in high-resolution localization microscopy", PhD Thesis, Doctor School of Physics, University of Szeged, dated 2014, 12 pp.

\* cited by examiner

MICROSCOPE FOR HIGH-RESOLUTION AND SPECIFIC ANALYSIS OF BIOLOGICAL SUBSTANCES, AND METHOD OF ANALYSIS

The subject of the invention is a microscope for high-resolution and specific analysis of biological substances, and a method of analysis.

More specifically, the invention is a microscope utilizing discrete illumination carrying no information on the color of the specimens and combining dark-field illumination technique with a high-powered, monochromatic, high-energy (short wavelength) light source and fluorescence microscopy. The microscope according to the invention enables up to one order of magnitude higher resolution than conventional light microscopes and 10-30% higher resolution compared to currently used dark-field microscopes (using white lighting) and provides a significantly sharper camera image visible to the naked eye. It applies the same discrete light source and a single filter to enable fluorescence microscopy, e.g. with FITC dye, thus, the stained portions and shapes of interest can be identified in the dark-field image and their accurate location can be monitored in comparison with unstained shapes. Conventional fluorescence microscopy enables only the observation of portions that have been visualized by staining but not the surroundings of it, whereas the microscope covered by the present invention shows the unstained portions, for instance, in blue and the stained portions, i.e. the ones the observer is looking for, distinctly in green if e.g. FITC dye is being used.

This invention covers also the method of analysis performed with the above-mentioned microscope.

It is known that special requirements are imposed on the morphological analysis of biological substances, as high-quality sharp images of ultra-high resolution are required to ensure that vital functions of living organisms in the specimen are traceable while in motion.

Ordinary light microscopy is usually suitable for the analysis of such substances if biological components in the sample are not damaged by the chemical stain used (if any) to make them visible (staining is required because the contrast between the biological components and their surroundings is usually low) and if the parts to be analyzed are not smaller than 0.3-0.4 micrometers (regarding their smallest dimension).

Staining and preparation methods, however, often make the sample unsuitable for the analysis of vital functions of moving biological components.

Ordinary light microscopes (with direct lighting, no dark-field illumination) have a resolution threshold that is proportional to the wavelength of the light used as per the following equation:

$$d = \frac{0.61 \times \lambda}{n \times \sin\theta}$$

where:
  d is the angular resolution (or limit of resolution),
  λ is the wavelength of light used,
  n·sin θ collectively: numerical aperture (n is the refractive index of the medium between the lens and the object and θ is the half-angle of the lens).

The equation above is applied as a static calculation in most specialized materials. This is a result of the fact that human brain wants to and is used to see everything in color; and this applies also to shapes that are colorless in themselves, hence potential solutions that disregard information on color have not even been considered. Additionally, the entire range of the color gamut is used for staining biological substances.

As a result of the two—technological and psychological—reasons listed above, microscopes dominantly use white light with an average wavelength of 550 nm depending on color temperature (and the wavelength usually has a wide spectrum and Gaussian distribution) and has an angular resolution of 400 nm, that is 0.4 micrometers, if using a high-quality lens. Increasing numerical aperture has been considered so far as the correct solution, namely the improvement of the lens or the increase of the refractive index (e.g. with an immersion lens).

We have concluded that the increase of the numerical aperture does not always provide a solution to improve analytical options, because—as we are going to elaborate it later—there is no direct light entering the lens in dark-field microscopy and if the numerical aperture is increased through either the refractive index or the characteristics of the lens, direct light will also enter the lens, which is a disturbing factor instead of being an advantageous factor increasing resolving power. This fact was verified with a high-quality microscope in dark-field operating mode and it was found that as low as 0.95 NA already produced a background bokeh effect and grey color instead of black was seen in the background.

If we were to disregard color as a feature that needs to be tested, there would be more options available to further reduce object size visible with the microscope. In theory, shortening the wavelength within the visible spectrum could offer a solution, however, no stand-alone solution has been found to date in literature or in practice.

The method of significantly shortening wavelengths outside the visible spectrum is applied in complex devices used for other purposes, however, it's application area is different from that of light microscopy and it involves the use of complex, large-scale and expensive equipment.

Specialists and researchers have been trying to use complex equipment in the area of light microscopy to get out of the scope of the aforementioned equation in an effort to achieve significantly higher resolution. Several other techniques have been used to create an image outside the scope of validity of the above-mentioned equation, including confocal microscopy, in which the sample inside the given field of view is illuminated point by point and a computer compiles the image. Therefore, the real resolution is the distance between the illuminated points (i.e. stepping size of the mechanism) instead of the value defined in the equation. However, as already mentioned above, these are extremely complex techniques that are capable of increasing resolution by up to one order of magnitude, but on the other hand, these are complicated (complex micromechanical-optical solutions are required) and asset-intensive, therefore very expensive and unsuitable to be used as an everyday testing method in the scientific world.

Therefore, in the case of conventional light microscopes, specialists do not possess any advisory notes or instructions that would enable them seek simple, everyday routine solutions, which would achieve a smaller rate of improvement compared to that achievable with modern methods, but they would still provide an improved testing environment in everyday practice compared to what has been achievable so far and there is an existing professional need for that. Increasing the resolution of the dark-field image by about 30% and the ability to achieve a sharper image is exactly what is needed for the analysis of certain living specimens.

The technical background of this invention, as summarized above, can be studied from the following academic literature:

Dr. Miklós Kellermayer: Biomedical light microscopy and computer image analysis, Ph.D. course, Doctoral School of Theoretical Medicine, SOTE József Sinkó: Analysis and correction of imaging and image reconstruction errors in high-resolution localization microscopy, PhD thesis, University of Szeged, TIK http://mogi.bme.hu/TAMOP/muszaki_optika/ch07.html#ch-VII.1.16 BME MOGI Department, Technical Optics, Chapter 7—The microscope as an optical system http://selmeczi.eu/david/diploma/diplomamunkanode19.html Fluorescent staining, Dávid Selmeczi's thesis One of the directions in development set by specialists in the given field regarding light microscopes is the further improvement of objective lenses and the construction of more expensive optics with higher numerical aperture (0.85→0.95 NA would theoretically improve resolution), however, these solutions focus on the analysis of colored objects with direct-light microscopy.

Another challenge specialists are facing is the improvement of imaging. A further issue is that, when light microscopy is used with white light, objects have a colored edge. This phenomenon is based on the fact, that lights of different wavelengths are refracted differently by the lenses. In order to correct it, objective lenses typically have a converging and a diverging lens installed behind each other. However, a maximum of 2 to 3 pairs of such lenses can be used in practice correcting the mistake for only a few wavelengths only (e.g. blue-green-red).

We asked ourselves the question: what happens if the development effort expended in resolution and imaging is taken towards a pathway specialists do not even think about, i.e. what happens if we relinquish the need for color images, which are generally irrelevant in the case of small objects (red blood cell morphology is specific and does not require the evaluation of red color and most human cells do not have a characteristic color).

If low-contrast biological substances need to be analyzed at angular resolution without colors and staining, it is possible to use a dark-field microscope. The Tyndall effect is the most intense in the case of objects having a size nearly equivalent to the wavelength of light, which is exactly around the angular resolution according to the above-mentioned equation. This enables the analysis of unstained specimens and, as mentioned above, since the color of most biological substances is irrelevant, no essential information is lost. Although the equation above can be used to determine that in general, resolution increases with the decrease of wavelength in microscopes (size of resolvable object is reduced), as far as we know, no one has ever studied the effect of it on imaging in the case of dark-field microscopy. As it has already been pointed out, the dark-field microscope functions based on a different effect, which is beyond the realm of microscopes. Therefore, there is no unequivocal equation to describe the combination of microscopes and the Tyndall effect. (It should also be noted that it is emphasized in the case of the Tyndall effect, that blue light is scattered more than red light, however, its relation with the size of the particles in the test sample is not mentioned as a major factor). There could have been several reasons why the relationship between the wavelength of light and the resolution in the case of dark-field microscopes has not been studied in more detail, including lack of motivation, unavailability of technology and the low lighting intensity of light sources in practice.

We have already analyzed the resolution of the dark-field microscope with a mercury-vapor lamp (which emits a shorter wavelength of blue light), however, we found that the lighting intensity had dropped so much that the camera automatically adjusted picture brightness and gain resulting in no significant difference, or rather a grainy image. Looking through the eyepiece, no major difference was observed. Therefore, it may have seemed that the above-mentioned equation is not valid in dark-field microscopy, which seemed to be logical, because the dark-field microscope itself contradicts the above-mentioned equation as it visualizes narrower objects than the angular resolution. It did not appear to be logical to us, because the Tyndall effect also depends on the wavelength meaning that it is the most intense, when the radius of analyzed particles and the wavelength of light are nearly identical, therefore, the wavelength needs to be shortened in order to reduce angular resolution. We have been using dark-field microscopes for decades, therefore, we have had the opportunity to test a number of cameras and light sources and we have been making conscious efforts to verify the phenomenon.

Another practical issue is the application of color cameras offered primarily by all manufacturers for dark-field analyses. In dark-field microscopes, dispersion occurs as a part of the system and it cannot be improved with the modification of the objective lens, which is the principal direction of recent developments for light microscopes. Dark-field microscopes, even if equipped with color-corrected (apochromatic) objective lenses, create color and rainbow edges around all objects, causing sharpness issues especially in narrower objects. The object seems to be less sharp on the edges even with black and white camera, however, in this case the edge is not colored but blurred.

Although black and white ultra-sensitive cameras are mainly applied in the field of astronomy, we started to use them in microscopes as color is an irrelevant information for us. However, it was also necessary to increase chip resolution further (3 sensors/pixel are normally used for color imaging hence chip resolution cannot be increased so remarkably). It should be noted that the system was not designed to improve absolute resolution as most researchers would do (megapixels, meaning the absolute number of pixels) but to improve the number of sensors/mm$^2$ in the chip, meaning pixel density. The smallest available pixel size in black and white cameras is approx. 4 microns, whereas the same is above 8 microns in many b&w and color cameras (experts did not consider this information when offering cameras), therefore, we have been able to quadruple pixel density. Having recognized this, the necessary resolution has become available to verify the suspected phenomenon.

The combination of monochromatic and short wavelength light was not mentioned in the literature. It is well-known that shortening the wavelength of light source improves resolution (https://www.doitpoms.ac.uk/tlplib/optical-microscopy/resolution.php, University of Cambridge, Optical Microscopy and Specimen Preparation, Resolution & Imaging), however, this phenomenon is known to exist in optical microscopes, whereas dark-field microscopes are outside the limits of such resolution. If monochrome light sources are sought, LED lamps will be offered. Here is an example of a commercially available product: https://blueboxoptics.com/wp-content/uploads/2019/06/niji-datasheet-BBO-NIJI-JUN-19-A.pdf (Blue box optics, LED Light Source for Microscopy). This light source is capable of achieving about one fifth of the light power compared to that of the light source we assembled—this will later play an important role in fluorescence. Additional references on using LED light sources: http://zeiss-campus.magnet.fsu.edu/articles/light-sources/leds.html (ZEISS Microscopy Online Campus, Light-Emitting Diodes), http://www.microbe-hunter.com/how-to-obtain-the-best-resolution-with-your-microscope/ (Microbehunter Microscopy, How to obtain the best resolution with your microscope). It can be observed that the combination of the two approaches focusing specifically on the improvement of image quality is neither mentioned in any references nor derivable from them. The literature is even more deficient in the case of dark-field microscopes.

The objective of this invention is to provide a simple and routinely accessible solution by making available a not too complex or costly construction and process for everyday practical use in an effort to achieve better results than those achievable with current techniques.

One major finding in relation to this invention focuses on the increase of resolution, namely, we realized that the wavelength according to the equation should be reduced to the shortest possible. This solution does not exist for microscope light sources as a separate light source of short wavelength, because the intensity of it would be insufficient, moreover, using white light is also not applicable as quite a powerful light source is required to provide a sufficiently bright image after letting only short wavelength light passing via an appropriate filter in the extreme intensity range (blue-violet).

A second finding that can result in a sharper image is that the wavelength range of light must be reduced as much as possible. Our previous experiments with a mercury-vapor lamp radiating only in a few discrete wavelength ranges should have resulted in sharper images in theory. However, luminous power—due to the features of the microscope and the characteristics of the lamp—was so low that the gain on the camera used for imaging had to be increased so much that the image has not become significantly sharper. We have concluded that avoiding dispersion, which is only possible with using monochromatic light in dark-field microscopes, enables us to capture sharper images.

The evolution of LED technology has enabled us to put the finding above into practice. Using a high-powered blue light source and a suitable camera (b&w camera applied in the field of astronomy), the phenomenon, i.e. resolution increases with shorter wavelength and dispersion ceases if monochromatic light is applied, has been verified.

Another light source used in our subsequent tests was a high-powered blue LED and the chosen unit was the most intense one with a wavelength of 450 nm (+/−10 nm). This is primarily used as lighting for crop production, radiation treatments and surveillance systems. Light sources available for microscopes provide one order of magnitude less energy.

As the majority of professionals are not interested in the development of dark-field microscopes, no one has ever come up with a similar solution or set preliminary expectations that inventors have suspected for decades based on the imagined boundary phenomena of physics (wider interpretation of resolution equation, dynamic interpretation of the Tyndall effect, the effect of dispersion on dark-field image quality).

The advantages of using monochromatic light of short wavelength as per the above invention are the following:
  short wavelength increases the angular resolution of the microscope
  monochromatic light provides a razor-sharp image due to the lack of dispersion
  the dark-field image has a pitch-black background because blue monochromatic light ensures that the light is emitted from the dark-field condenser in a greater angle compared to the axis so that no direct light enters the objective (even if the objective has a larger numerical aperture). For the same reason, objectives with a larger numerical aperture can also be applied without direct light entering the objective.
  light with a wavelength of 450 nm amplifies the Tyndall effect just around the angular resolution of the microscope ($\lambda \sim r$, where r is the radius of the visible objective according to the phenomenon), especially in the case of smaller objects, making small or narrow bacteria, such as spirochetes, mycoplasma, etc., more visible.

According to this invention, the solution enables additional specific applications, as follows.

If living components are identified in the biological specimen, it can be a matter of interest to determine, whether they are identical to a known living organism containing specific proteins. Antibodies marked with fluorescent dye can make them visible for specific identification in the case of microscopes. It is a common practice in fluorescence microscopy to use antibodies marked with FITC or other dyes.

Fluorescence microscopes are constructed to use excitation light (e.g. 450 nm blue) to illuminate the specimen from above and to detect the resulting fluorescence (e.g. 535-550 nm green) from above after filtering out the wavelength of the illumination light, therefore, nothing else but the light of excited dye is visible.

An essential factor is to prevent direct light, e.g. along with blue light, from entering the objective directly. Although this is commonly achieved by using overhead illumination, light may be supplied from any direction, even from the bottom in a tilted direction like in the case of the condenser in dark-field microscopes.

When using our microscope with blue light illumination (additionally equipped with a fluorescent attachment with top lighting) on specimens marked with fluorescent dye, a surplus effect was observed unexpectedly. If the lamp of the fluorescent attachment is turned off and the blue LED light with a wavelength of 450 nm is used along with a dark-field condenser, only the light scattered as a result of Tyndall effect and the fluorescent green light excited by blue light will be visible, whereas the incident light will not be visible. If a green filter is inserted in front of the eyepiece or the camera to filter out blue illuminating light, it enables us to identify objects specifically stained with the specified antibody as only fluorescent green objects will be visible.

In the light of the above, the essence of the microscope according to the invention is that it comprises a power supply unit attached to the microscope lamphouse capable of generating constant current (to supply a monochromatic, preferably LED light source), a system of mirrors and illuminating optics, a collector lens placed between the monochromatic light source, a tube acting as a "collimator" to collect the LED light into the collector lens, a dark-field condenser and objective including an in-between space to accommodate the stained biological specimen, a surveillance camera or eyepiece, and a removable color filter placed between the objective and the surveillance camera or the eyepiece.

As a conclusion, the invention itself is a microscope for high resolution and specific analysis of biological substances characterized by a power supply unit capable of generating constant current attached to the microscope housing; a system of mirrors and illuminating optics; a collimator placed between a monochromatic light source emitting light in a very narrow wavelength range and the collector lens; a dark-field condenser and objective including an in-between space to accommodate the stained biological specimen; and a surveillance camera or eyepiece, and a removable color filter placed between the objective and the surveillance camera or the eyepiece.

For the purpose of the invention, to take an example, bandwidth (the range of wavelengths within which light intensity drops to half) was set at −±10 nm, or more preferably ±1-5 nm without limiting ourselves to do so.

The collector lens is preferably the original lens provided with the original lamphouse of the selected microscope, the monochromatic light source is preferably a blue, 450 nm LED light source set at a maximum current of 3000 milliamperes and luminous power of approx. 900-1500 lumens. The LED light source is preferably attached to a heat sink practically having a surface area of 35 cm² as a minimum. The center of the LED chip is positioned precisely at the focal point of the lens.

The collimator is preferably a tube with dull white internal surface and an internal diameter matching that of the original collector lens in the lamp. Its length is equal to the focal length of the lens (since it is placed between the lens and the heat sink carrying the LED chip). The white tube and the dull surface are required to maximize light reflection: the LED light source practically emits light in space in a solid angle nearly equivalent to a hemisphere. Without a collimator tube and lighted from the typical focal length of lenses applied in microscope lamphouses, approximately 10-20% of that light would enter the surface of the lens. The collimator tube is supposed to reflect as much light as possible to the lens surface via single reflection or multiple reflections. Surprisingly, contrary to solutions pro-posed by specialists (e.g. bright internal surface), the dull white surface resulted in the best effect: every single point of the dull white surface acts as an individual light source reflecting light primarily towards the lens to ensure more light entering the lens directly and via additional reflections, whereas in the case of bright surfaces, light is reflected only in an angle equivalent to the angle of incidence, hence the beam is reflected multiple times before reaching the lens unless it is entirely reflected off the lens surface due to high angle of incidence.

In order to promote better understanding, the solution according to this invention is represented in figures below and followed by examples. It should be noted that neither the figures nor the examples restrict the invention to the form of implementation or the procedure specifically presented herein.

Figure 2:
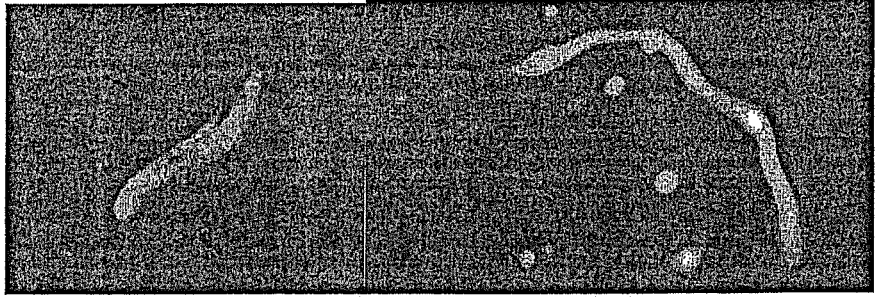

Therefore, the figures shall represent the followings:

FIG. 1 is the schematic, perspective view of the solution according to the invention, FIG. 2 shows the image of a specimen stained with fluorescent dye in the microscope. Although the fluorescent image is represented in black and white, it unequivocally shows the characteristic shape of *Borrelia* and the location of various cell portions marked with the antibody.

Figure 3:
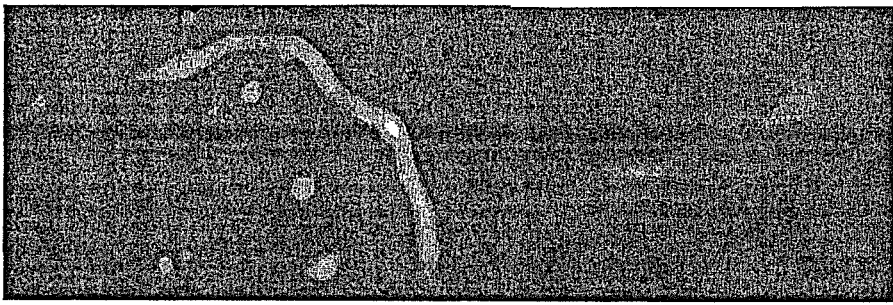

FIG. 3 represents a dark-field camera image visible in the microscope without using fluorescent staining or green filter. The image captured with the microscope arrangement according to FIG. 1 is shown on the left hand side of the figure, whereas the image captured with a dark-field microscope with conventional white light illumination is shown on the right hand side. The difference between the images is remarkable: whilst the image on the left is sharp with a black background, showing the characteristic spirals of *Borrelia*, the image on the right is "grainy" and blurry, its resolution is low and sharpness is insufficient due to the application of white light, the background is greyish.

The special light source shall be prepared as follows:

The halogen or LED light is removed from the microscope housing. A power supply unit capable of generating constant current is attached to the housing (not shown in the figure). The following components shall be installed in the housing:

The original collector lens 3 of the lamphouse;

the monochromatic light source 1, in this case, blue LED light source (preferably 450 nm, set at a maximum current of 3000 milliamperes and luminous power of approx. 900-1500 lumens and luminous power is controlled by adjustable current) attached to a heat sink practically having a surface area of 35 cm² as a minimum—the LED chip center is positioned precisely at the focal point of the collector lens 3;

the collimator 2 is preferably a tube with dull white internal surface and an internal diameter matching that of the original collector lens in the lamp. Its length is equal to the focal length of the collector lens 3 (since it is placed between the lens and the heat sink carrying the LED chip). The horizontal beam of light set into parallel direction by the collector lens 3 is directed into vertical direction by a set of mirrors 4 and lighting optics.

The dark-field condenser 5 is positioned above the aforementioned components, the stained biological specimen 6 is to be placed above it and observed through the objective 7 equipped in this case with a green color filter 8 with a surveillance camera 9 or an eyepiece 10.

In the case of using another fluorescent stain the microscope can be constructed to apply different excitation LED wavelength (e.g. UV or green), to use a UV permeable lens system or a different filter (e.g. red).

The invention aims the development of a method to analyze biological specimens with fluorescent staining, making it unnecessary to capture moving cells in the specimen enabling their analysis during movement. The method consists of analyzing the biological contents of the specimen in growing medium in liquid state after the addition of antibodies marked with fluorescent stain, using the above-mentioned microscope according to the invention. The analysis should preferably be performed on a specimen in DualDur cell culture medium or in any other growing medium of low conductivity. DualDur cell culture medium is registered under the same trade name and its components are known from the Hungarian patent specification HU220169.

The method according to the invention consists of analyzing the biological contents of the specimen in growing medium in liquid state after the addition of an antibodies marked with fluorescent stain, using the microscope according to the invention.

The analysis is performed on a specimen in DualDur cell culture medium or in any other growing medium of low conductivity.

The following steps are to be followed during staining the specimen according to the invention:

The specimen is provided in a growing medium in liquid phase to ensure sufficient living conditions and there should be a sufficient level of concentration of the biological substance in the specimen (a minimum of 3 to 5 microorganisms/microliter);

The specimen is mixed slowly in a test tube with a tube shaker preferably set to 3-500 rpm;

Antibodies binding to the biological substance to be detected in the biological sample and marked with fluorescent dye (preferably FITS or other dyes excitable with blue light) are added to the biological substance in a ratio of 1 to 30%. The dye may be diluted with growing medium as necessary.

The dye is added to the specimen drop by drop in more phases.

The specimen is mixed for additional 3 to 30 minutes.

Optionally, fluorescence fixative may be added to the specimen.

If the specimen is put in a growing medium or liquid with low ionic strength (low conductivity, preferably 2-3 mS), the antibodies can bind easier to proteins (antigen) to be marked and this unexpected surplus effect was experienced during *Borrelia* staining in a cell culture medium, registered under the trade name of DualDur. This phenomenon is essential to preserve motion in the specimen and to ensure that no pre-fixation is required on a specified surface, which is a common procedure for similar stains.

Incubation is applied at a temperature of 30 to 36° C. for 15 to 30 minutes to enhance antibody binding.

A sample of 2-4 microliters is transferred from the liquid to a slide and sealed with a cover slip. It is placed in the special microscope according to the present invention.

During this method, contrary to similar staining methods, the biological substances are not bound to a surface and not frozen, the cell membrane is not made permeable before staining, hence only a small amount of fluorescent stain is bound, not preventing the biological substance from moving. Although this would remain invisible in most optical systems, the very powerful LED excitation light and the excellent objective designed for fluorescent microscopy enables the sensitive camera to visualize the fluorescent stained biological substance and its movement.

EXAMPLES

Example 1

The analysis is a specific visual technique showing parallel the image and the movement of pathogens in the dark-field microscope and identifies them as being *Borrelia burgdorferi* s.l. (sensu lato, in the broad sense) at a confidence level of approx. 99%.

Required chemicals and equipment are as follows:

Polyclonal antibodies marked with fluorescent dye are applied for the analysis. Contrary to common applications, *Borrelia* suspected to be present in the specimen are not required to be bound to a surface, but they are stained in a liquid phase using the special technique described above. The blood sample is obtained in a modified DualDur reagent keeping Spirochetes (including *Borrelia*) alive for up to 3 weeks, and having low ionic strength that helps the antigens binding to the antibodies. The sample is concentrated by DualDur double centrifugation and the second sediment is loaded in a shaker set at a speed of 300 rpm. As per the above description, polyclonal *Borrelia* antibodies marked with FITC are added to this liquid. This way their specific marking is ensured without the restriction of movement. Our pilot experiments showed unequivocal morphological match between *Borrelia* seen in the dark-field microscope and the stained *Borrelia* moving underneath the fluorescent microscope on the very same slide.

This special analysis offers all the advantages of fluorescence microscopy, which carries diagnostic value in many countries—with very low sensitivity. It is because *Borrelia* concentration is low in the blood, and to increase its level and the number of surface antigens, it is commonly combined with culturing. To increase concentration, the normally applied DualDur processing and concentrating method was applied before staining. Another reason for low sensitivity in the case of conventional fluorescence staining is that *Borrelia* is relatively vulnerable and can easily be washed off the surface during conventional staining methods. According to this new method, staining is performed in liquid phase with higher bacterial concentration. Low ionic strength, incubation and higher bacterial concentration are all essential to stain sufficient amount of bacteria.

The cross-reactivity of staining affects *Borrelia* and certain *Treponema* strains. Firstly, based on in-vitro pilot experiments, *Treponema* could be distinguished morphologically from *Borrelia* strains with a success rate of more than 80%, secondly, the prevalence of *Treponema* in the blood is one or two orders of magnitude lower, thirdly, subjects carrying *Treponema* in identifiable amounts in the blood would suffer from more serious symptoms than in the case of *Borrelia* infection that can be distinguished by a physician. Another cross-reacting *Borrelia* is the pathogen of relapsing fever (*Febris recurrentis*), the prevalence of which, however, cannot be detected within the geographic area of our analysis. Therefore, a positive staining result reflects *Borrelia* with high probability.

Example 2

Enhancement of dark-field camera image and improvement of perception through the eyepiece. The dark-field microscope is equipped with a high-power (preferably 900 lumens), short wavelength and monochromatic (preferably 450 nm+/−10 nm) light source emitting blue light. By omitting the green filter according to the arrangement in FIG. 1, the image of the dark-field microscope will become significantly sharper both in the camera and in the eyepiece.

FIG. 3 shows the camera image according to the microscope arrangement in FIG. 1, using monochromatic blue lighting in dark-field arrangement (left hand side) and using dark-field microscope with white lighting (right hand side).

As mentioned above, the microscope according to this invention enables up to one order of magnitude higher resolution than conventional light microscopes and 10-30% higher resolution compared to currently used dark-field microscopes (using white lighting) and provides a significantly sharper camera image. It applies the same discrete light source to enable fluorescence microscopy, e.g. with FITC dye, using a single filter, thus it becomes possible to observe stained portions and features of interest in the dark-field image and their accurate location can be monitored compared to unstained features. Conventional fluorescence microscopy enables only the observation of portions visualized by staining but not the surroundings, whereas the microscope in the present invention shows unstained portions, for instance in blue and stained portions, i.e. the ones the observer is looking for, distinctly in green e.g. in the case of FITC staining.

The invention claimed is:

1. A microscope for high-resolution dark field and specific fluorescence analysis of biological substances at the same time, comprising: a microscope housing; a power supply unit capable of generating constant current attached to the microscope housing; a set of mirrors; a monochromatic light source of a wavelength of 450±10 nm or a UV light source, the monochromatic light source emitting blue or green light or the UV light source emitting UV light; a collimator, which is in the shape of a tube, and being placed between the monochromic light source or the UV light source and a collector lens; a dark-field condenser and an objective including an in-between space between the dark-field condenser and the objective to accommodate a stained biological specimen; a surveillance camera or eyepiece; and a removable color filter between the objective and the surveillance camera or the eyepiece.

2. The microscope according to claim 1, wherein the monochromatic light source is a blue LED, having a wavelength of 450 nm, with a maximum current draw of 3000 milliamperes, set at a luminous power of 900-1500 lumens.

3. The microscope according to claim 1, wherein the collector lens is the collector lens of a lamphouse of a dark-field microscope.

4. The microscope according to claim 1, wherein an LED light source is used as the monochromatic light source, the LED light source is attached to a heat sink having a minimum surface of approximately 35 cm$^2$.

5. A microscope for high-resolution dark field and specific fluorescence analysis of biological substances at the same time, comprising: a microscope housing; a power supply unit capable of generating constant current attached to the microscope housing; a set of mirrors; a monochromatic light source of a wavelength of 450±10 nm or a UV light source, the monochromatic light source emitting blue or green light or the UV light source emitting UV light; the collimator is in the shape of a tube placed between the monochromic light source or the UV light source and a collector lens; a dark-field condenser and an objective including an in-between space between the dark-field condenser and the objective to accommodate a stained biological specimen; a surveillance camera or eyepiece; and a removable color filter between the objective and the surveillance camera or the eyepiece, wherein the collimator has a dull white internal surface and an internal diameter matching that of the collector lens and its length is equal to the focal length of the collector lens.

6. A method for the analysis of biological specimens with fluorescent staining, comprising: analyzing biological contents of a specimen in a growing medium in liquid state after the addition of antibodies marked with fluorescent stain, using the microscope according to claim 1.

7. The method according to claim 6, wherein the analysis is performed on the specimen in a cell culture medium.

8. The microscope according to claim 1, wherein the dark-field condenser is a cardioid dark-field condenser.

9. The microscope according to claim 5, wherein the monochromatic light source is a blue LED, having a wavelength of 450 nm, with a maximum current draw of 3000 milliamperes, set at a luminous power of 900-1500 lumens.

10. The microscope according to claim 5, wherein the collector lens is the collector lens of a lamphouse of a dark-field microscope.

11. The microscope according to claim 5, wherein an LED light source is used as the monochromatic light source, the LED light source is attached to a heat sink having a minimum surface of approximately 35 cm$^2$.

12. The microscope according to claim 5, wherein the dark-field condenser is a cardioid dark-field condenser.

13. A method for the analysis of biological specimens with fluorescent staining, comprising: analyzing biological contents of a specimen in a growing medium in liquid state after the addition of antibodies marked with fluorescent stain, using the microscope according to claim 5.

14. The method according to claim 13, wherein the analysis is performed on the specimen in a cell culture medium.

* * * * *